US008337910B2

(12) United States Patent
Avila

(10) Patent No.: US 8,337,910 B2
(45) Date of Patent: Dec. 25, 2012

(54) HERBAL FORMULATION FOR THE TREATMENT OF BONE FRACTURES AND OSSEOUS DEFECTS

(76) Inventor: Alfredo Avila, Estado Aragua (VE)

( * ) Notice: Subject to any disclaimer, the term of this patent is extended or adjusted under 35 U.S.C. 154(b) by 0 days.

(21) Appl. No.: 12/961,636

(22) Filed: Dec. 7, 2010

(65) Prior Publication Data

US 2011/0076345 A1 Mar. 31, 2011

Related U.S. Application Data

(62) Division of application No. 12/078,509, filed on Apr. 1, 2008, now Pat. No. 7,871,648.

(60) Provisional application No. 60/907,451, filed on Apr. 2, 2007.

(51) Int. Cl.
*A61K 36/30* (2006.01)
(52) U.S. Cl. .................................. 424/725; 424/401
(58) Field of Classification Search .......... None
See application file for complete search history.

(56) References Cited

U.S. PATENT DOCUMENTS

| 5,525,618 | A | 6/1996 | Shudo |
| 2003/0203843 | A1 | 10/2003 | Pena |
| 2004/0052872 | A1* | 3/2004 | Ionascu ............... 424/725.1 |
| 2005/0014687 | A1 | 1/2005 | Anderson |
| 2005/0106266 | A1 | 5/2005 | Levinson |
| 2005/0215493 | A1 | 9/2005 | Miyake |
| 2007/0020724 | A1 | 1/2007 | Ruben |

FOREIGN PATENT DOCUMENTS

| GB | 2311009 | 9/1997 |
| WO | 2006032091 | 3/2006 |

OTHER PUBLICATIONS http://web.archive.org/web/20050307081419/http://www3.telus.net/drdoan/pessary.html—internet archived version from Mar. 2005.*
Lyle (Physio-Medical Therapeutics, Materia Medica and Pharmacy. 1932. National Association of Medical Herbalists, Ltd: London. "*Phytolacca decandra*" section).*

* cited by examiner

*Primary Examiner* — Susan Hoffman
(74) *Attorney, Agent, or Firm* — Yancy IP Law, PLLC

(57) ABSTRACT

An herbal formulation including *Symphytum Officinalis* extract and *Phytolacca Decandra* extract may be combined to treat bone fractures and osseum defects. Specifically, the herbal formulation provides for the regeneration of osseum tissue for treating bone defects such as imperfect osteogenesis, pseudo-arthrosis infected or not, bone union delay of fractures, osteoporosis, osseum tumors, aneurismatic osseum cyst, and myeloma multiple.

6 Claims, 16 Drawing Sheets

HERBAL FORMULATION FOR THE TREATMENT OF BONE FRACTURES AND OSSEOUS DEFECTS

CROSS REFERENCE TO RELATED APPLICATIONS

This is a divisional application of Ser. No. 12/078,509 filed Apr. 1, 2008, now U.S. Pat. No. 7,871,648, the contents of which are incorporated herein by reference. This application claims the benefit, under 35 U.S.C. 119(e), of U.S. Provisional Application No. 60/907,451 filed Apr. 2, 2007, the contents of which are incorporated herein by reference.

FIELD OF THE INVENTION

The present invention relates generally to an herbal formulation including *Symphytum Officinalis* extract and *Phytolacca Decandra* extract for the treatment of bone fractures and osseum defects.

BACKGROUND OF THE INVENTION

Healing of bone lesions is one of the inherent properties of a living organism, while the regenerative potency of the bone tissue is practically limitless. Complete and perfect reunion of bone fragments is unattainable without formation of a regenerated osseous tissue (callus) that fills up the gap between the fragments of the fractured bone. The process of reunion proceeds in several steps, i.e., first a connective layer arises around the fracture, comprising the components liable to calcify to form a callus that will turn into the bone tissue under the normal course of the fracture reunion process, which exhibits characteristic biochemical and physiological properties.

For many years, the scientific community has been conducting research for medical drugs for the treatment of bone fractures not only to consolidate the bones, but to reduce the time estimated for healing the bones, normally 3 to 6 months. Additionally, open fractures have the added variable of complications due to the possibility of infection. This can occur directly from infection agents due to poor aseptic conditions of surgical centers in the case of management of medical instruments. This infection variable is present in as many as 40% of the cases avoiding the consolidation of the bones and consequently leading to the disability of the patient who has suffered an accident.

The use of synthetic material, such as metal plates, screws and other external fixers, has improved the consolidation process for bones. However, these material do not prevent union delays and pseudo-arthrosis which continue to be frequent and an unsolvable problem.

In the osteogenesis process, two factors are of primary concern: the inorganic and organic compound. Research has demonstrated the osseous tissue consists of organic matter (30 percent), mineral components (60 percent) and water (10 percent). The osseous organic matter is known to consist of collagen (95 percent), while as little as 5 percent accounts for other compounds. The mineral, or inorganic, constituent of a bone is in effect the crystals of hydroxyapatite formed by calcium and phosphorus salts. These crystals are the building materials that give consistency, resistance and strength to the osseum tissue which in most cases, due to the biological and biochemical dysfunction in the human body, the amounts needed can decrease and cause weaknesses that make the bones susceptible to damage coming from external sources and result in the appearance of fractures. The organic compound is represented by Collagen Type I, para-thromone and Vitamin D as is well known and studied. Collagen Type I is basically the principal element present in the Osseum Matrix and is formed by proteins encoded by CO1A1 and CO1A2 genes and provides a "cement" where the crystal calcium and phosphorus salt, i.e. hydroxyapatite, place one over the other until a resistant osseum tissue is formed. The aberrations (more or less 130) on these genes produce disturbances on the formation not only related to quantity but quality of Collagen type I which have been the studies of numerous studies conducted on imperfect osteogenesis, but not in fractures coming from another causes.

In addition to fractures resulting from outside causes, several diseases and defects of the bone tissue result in weakened and fracture-prone bones. Such diseases and defects include osteomyelitis, pseudoarthrosis, osteoporosis, osseum tumors, and imperfect osteogenesis. Furthermore, union delay of fractured bones is a condition that afflicts many people.

As an alternative to traditional medicine, many people find comfort from various ailments from herbal formulations and extracts. Comfrey, also known as *Symphytum officinalis*, is a member of the Boraginaceae or Borage family known for treating various ailments. Poke, also known as *Phytolacca decandra*, is a member of the Phytolaccaceae or Pokeweed family and is known to treat various conditions, including use as an anti-microbial compound. These herbal ingredients have also been known as ingredients in cosmetic compositions in combination with other herbal and chemical ingredients.

SUMMARY OF THE INVENTION

It has been unexpectedly discovered that an herbal formulation including *Symphytum Officinalis* extract and *Phytolacca Decandra* extract may be combined to treat bone fractures and osseum defects. These ingredients positively regulate the osteogenesis process making CO1A1 and CO1A2 genes increase encoding of the chains of Collagen Type I, by correcting the biological aberrations that permit the formation of a major quality and quantity of collagen. The genes CO1A1 and CO1A2 are located on chromosomes 7 and 13 and are responsible for encoding pro-collagen type I and BCRA1 acting over organic compounds of the osteogenesis process.

A pharmacologically effective amount of *Symphytum Officinalis* extract and a pharmacologically effective amount of *Phytolacca Decandra* extract, preferably in combination with Magnesium Chloride USP, Absolute Ethanol, and Sacrose/Lactose are provided to the patient as an herbal formulation. The herbal formulation may be delivered to the patient in any medically acceptable manner including, but not limited to, ingestion or topical application The ingredients are preferably ingested by the patient to treat a wide variety of bone fractures and bone defect related diseases including, but not limited to, osteomyelitis, pseudoarthrosis (infected or not), bone union delay of fractures, osteoporosis, osseum tumors and imperfect osteogenesis. The ingredients catalyze the osteogenesis process for each osseum defect and regenerate the osseum tissue, specifically aneurismatic osseum cyst and multiple myeloma, resulting in an increased mineral density of the bone. The herbal formulation is preferably presented to the patient in the form of a capsule or tablet. However, the herbal formulation may be applied topical in cases of ulcers produced by osteomyelitis. Alternatively, the herbal formulation may be supplied to the patient in the form of a dermal patch.

The present herbal formulation includes a pharmacologically effective amount of *Symphytum Officinalis* extract and a pharmacologically effective amount of *Phytolacca Decandra* that has been found to have regenerating and anti-litical properties when used on the human body and animals. This herbal formulation quickly forms osseum callus to increase mineral density and avoid cellular division of negative and positive gram bacteria, including the pseudomoma aeruginosa, currently present in infected bones, including numerous pathologies derived from aberrations of genes COL1A1, COL1A2 and BRCA1.

BRIEF DESCRIPTION OF THE SEVERAL VIEWS OF THE DRAWINGS

The features and advantages of the present invention will become apparent from the following detailed description of a preferred embodiment thereof, taken in conjunction with the accompanying drawings, in which.

DETAILED DESCRIPTION OF THE INVENTION

Figure 1B:
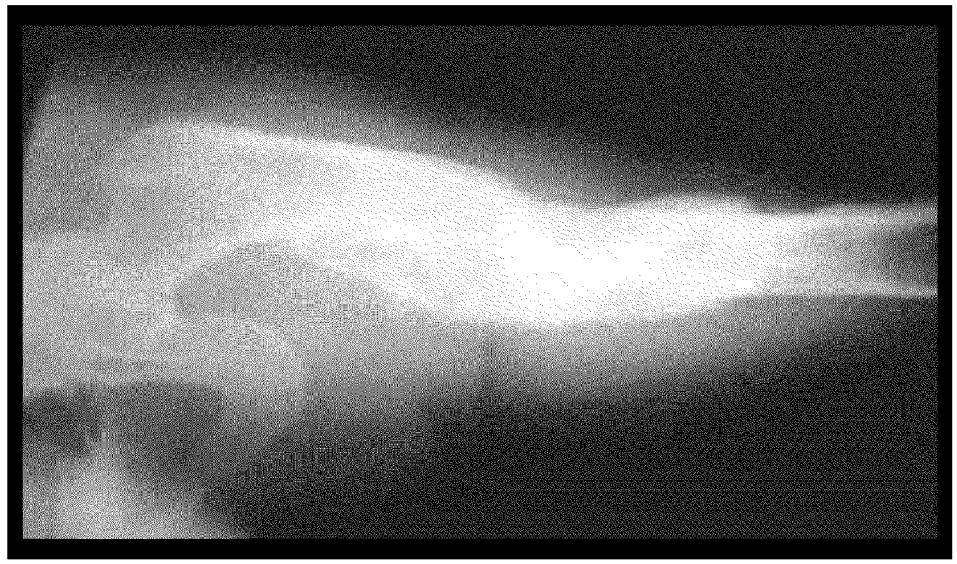
FIG. 1B is an X-ray of the femur of a 36 year old patient suffering from pseudoarthrosis without infection after treatment in accordance with the present invention.

A natural herbal formulation including a pharmacologically effective amount of *Symphytum Officinalis* extract and a pharmacologically effective amount of *Phytolacca Decandra* extract is supplied to a patient for treatment of bone fractures and bone-related diseases and defects. In a first embodiment, the herbal formulation may include less than 0.05 cc *Symphytum Officinalis* extract and less than 0.04 cc *Phytolacca Decandra* extract. In another embodiment, the herbal formulation may include 0.02-0.05 cc *Symphytum Officinalis* extract and 0.01-0.04 cc *Phytolacca Decandra* extract The herbal formulation catalyzes the formation of osseum callus and new osseum tissue. In addition to *Symphytum Officinalis* extract and *Phytolacca Decandra* extract, the herbal formulation preferably includes magnesium chloride USP. In a preferred embodiment, the herbal formulation further includes absolute ethanol (or ethyl alcohol) and sacrose/lactose. The active ingredients utilized in the present herbal formulation, *Symphytum Officinalis* extract and *Phytolacca Decandra* extract, and Magnesium Chloride USP are readily available in herb stores and through herb distributors such as Frontier Herbs, Norway, Iowa 52318 and BIOTECHNOQUIMICA Caracas, Venezuela. The herbal formulation may be administered to a patient with or without additional vitamins supplements. Specifically, the herbal formulation may provide beneficially results without the addition of calcium-based vitamin supplements. In a preferred method of using the present herbal supplement, the formation of osseum callus and new osseum tissue is provided with a normal diet of calcium that does not include calcium-based vitamin supplements.

The preferred embodiment of the herbal formulation includes *Symphytum Officinalis* extract and *Phytolacca Decandra* extract, absolute ethanol, magnesium chloride USP, and sacarose/lactose in the following amounts:

| | |
|---|---|
| *Symphytum Officinalis* extract | 0.02 cc |
| *Phytolacca Decandra* extract | 0.01 cc |
| Absolute Ethanol | 100 cc |
| Magnesium Chloride | 2 grams |
| Sacarose/lactose and other excepients | 1000 grams |

A preferred process for making the herbal formulation includes diluting 0.02 cc of the extract or Mother tincture of *Symphytum Officinalis* and 0.01 cc of *Phytolacca Decandra* in 100 cc of Absolute ethanol and mixing for 5 minutes. Once mixed, two grams of magnesium chloride USP is added to the mixture and mixed until a homogeneous and consistence mixture is formed. The contents are then spread over the sacarose/lactose and allowed to dry at ambient temperature. Once dried, the ingredients are again mixed, and other dietary supplements may be added to prepare the capsules for ingestion. In the case of tablets, acceptable stabilizers and emulsifiers may be added to form the tablet.

This herbal formulation may be provided to human and animals to treat bone fractures or bone related defects due to bone disease. It is understood that the herbal formulation acts as a catalyzer for the osteogenesis process. Some of the bone diseases that are treated using this herbal formulation include, but are not limited to, imperfect osteogenesis, pseudoarthrosis (infected or not), bone union delay of fractures, osteoporosis, osseum tumors, specifically the aneurismatic osseum cyst and myeloma Multiple.

To demonstrate the principal properties of this herbal formulation clinical controlled trials have been conducted. It should be understood that the following clinical trial represents only a sample of the herbal formulation of the present invention. One of ordinary skill in the art would understand that certain modification could be made to the herbal formulation without departing from the scope of the present invention.

Materials and Methods:

The clinical trials included a capsule having 0.02 cc *Symphytum Officinalis* extract; 0.01 cc *Phytolacca Decandra* extract; 100 cc absolute ethanol; and 2 grams Magnesium Chloride. In order to demonstrate the effectiveness of the present herbal formulation, X-rays of bone segments were taken before and after treatment. These X-rays prove that the present herbal formulation is beneficial for treating bone fractures and bone defects related to various forms of bone disease. The herbal formulation accelerated the new osseous tissue formation in the osseous fractures with delay of consolidation, pseudoarthrosis infected and not infected, osteomyelitis and Osteogenesis imperfecta. This herbal formulation is a biomaterial without secondary effects.

Figure 1A:
FIG. 1A is an X-ray of the femur of a 36 year old patient suffering from pseudoarthrosis without infection prior to treatment.

To participate in this study, a sample of 94 patients was taken that meet the established parameters of inclusion of protocol to whom the herbal formulation was administered without knowledge of their physician on which patients took biomaterial and which took the placebo. The regime for the clinical trials generally included one capsule or tablet per day to treat fractures and osteomielitis. Although, one capsule or tablet every two days is acceptable for osteoporosis and osteopenia. The clinical trials were separated into eight groups as follows:

Group I: Psuedoarthrosis not infected
Group II: Pseudoarthrosis infected
Group III: Delay of Surgical Consolidation
Group IV: Simple Fractures Not Surgical
Group V: Osteogenesis Imperfecta
Group VI: Osseous Tumors
Group VII: Prosthesis
Group VIII: Osteoporosis and Osteopenia Group I This clinical trial group included 12 patients diagnosed with Pseudoarthrosis without infection of which obtained callus osseous radiology visible. The patients had one capsule or tablet per day during 3 consecutive months. The results are as follows:

25% (3 patients) responded within 6 weeks
25% (3 patients) responder within 8 weeks
33% (4 patients) responded within 12 weeks
17% (2 patient) responded within 4 weeks The average number of weeks to obtain significant clinical and radiological changes was 8.5 weeks. The control was without clinical or radiological changes. FIG. 1A is an X-ray of a 36 year old patient prior to treatment. FIG. 1B is an X-ray of the same 36 year old patient after 12 weeks of treatment using the herbal formulation. As you can see from the X-ray bone tissue has grown to cover the fracture.

Figure 2B:
FIG. 2B is an X-ray of the lower leg of a 36 year old patient suffering from pseudo-arthrosis with infection after treatment in accordance with the present invention.
Figure 2A:
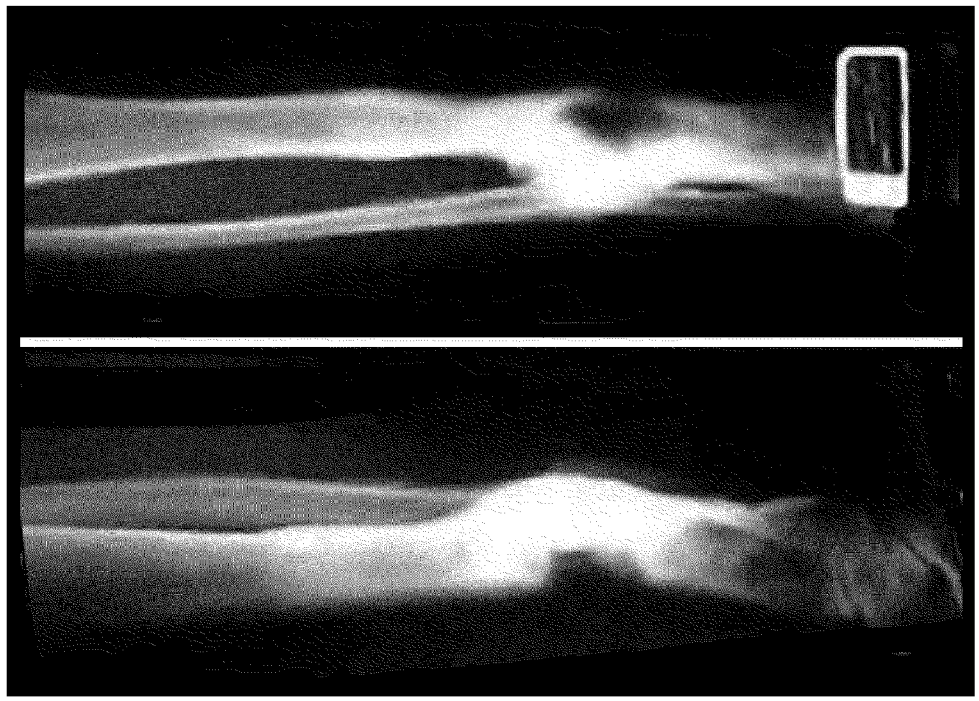
FIG. 2A is an X-ray of the lower leg of a 36 year old patient suffering from pseudo-arthrosis without infection prior to treatment.
Figure 3B:
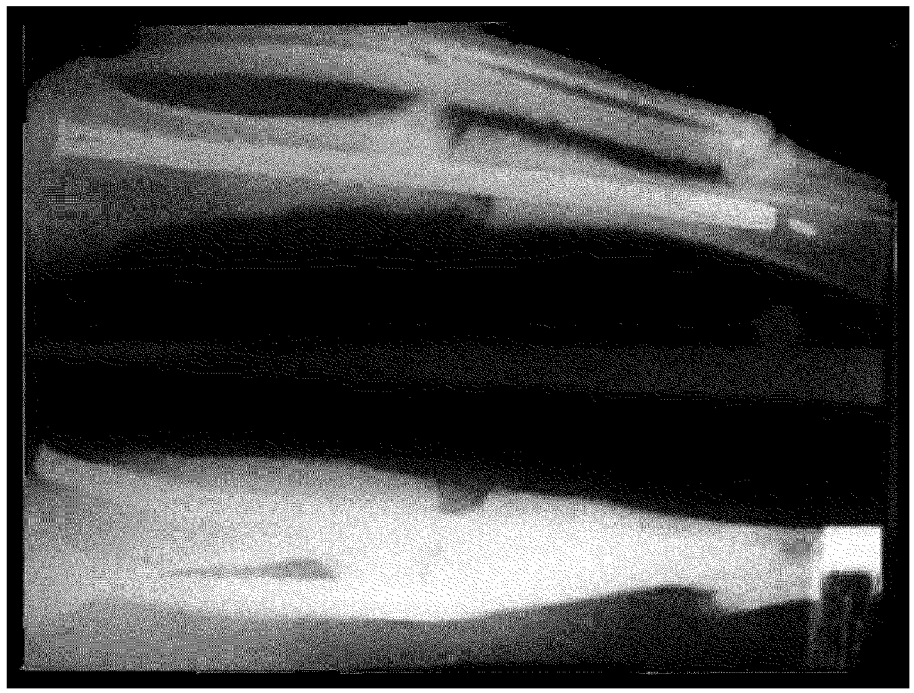
FIG. 3B is an X-ray of the lower leg of a 31 year old patient suffering from pseudo-arthrosis with infection after treatment in accordance with the present invention.
Figure 3A:
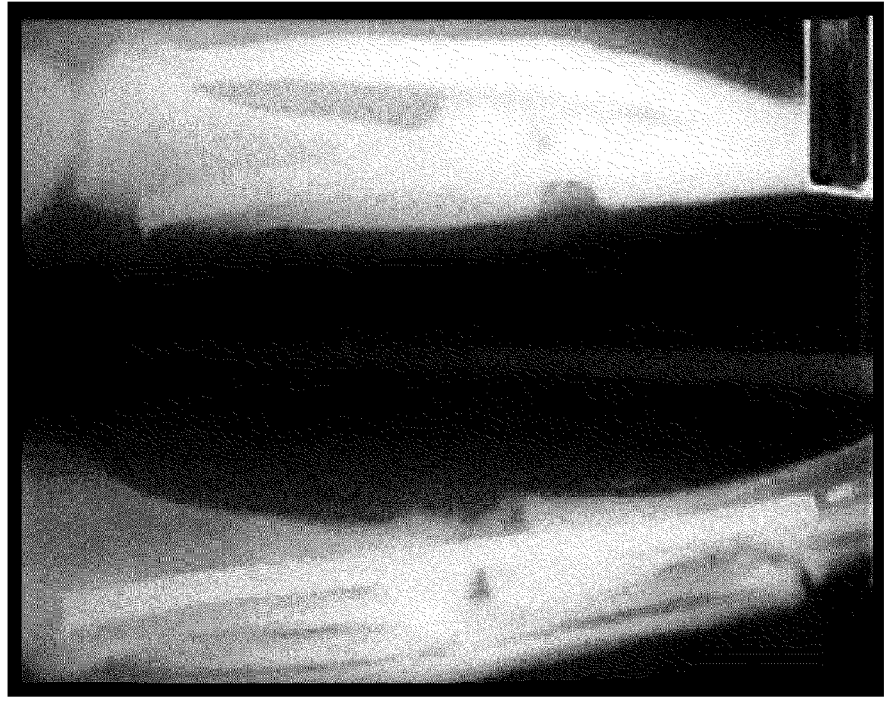
FIG. 3A is an X-ray of the lower leg of a 31 year old patient suffering from pseudo-arthosis with infection prior to treatment.
Figure 4B:
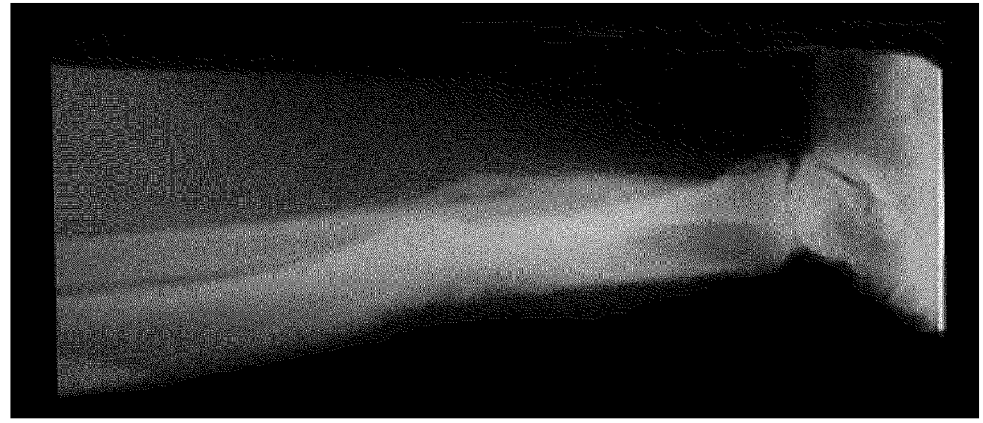
FIG. 4B is an X-ray of the lower leg of a 41 year old patient suffering from pseudo-arthrosis with infection after treatment in accordance with the present invention.
Figure 4A:
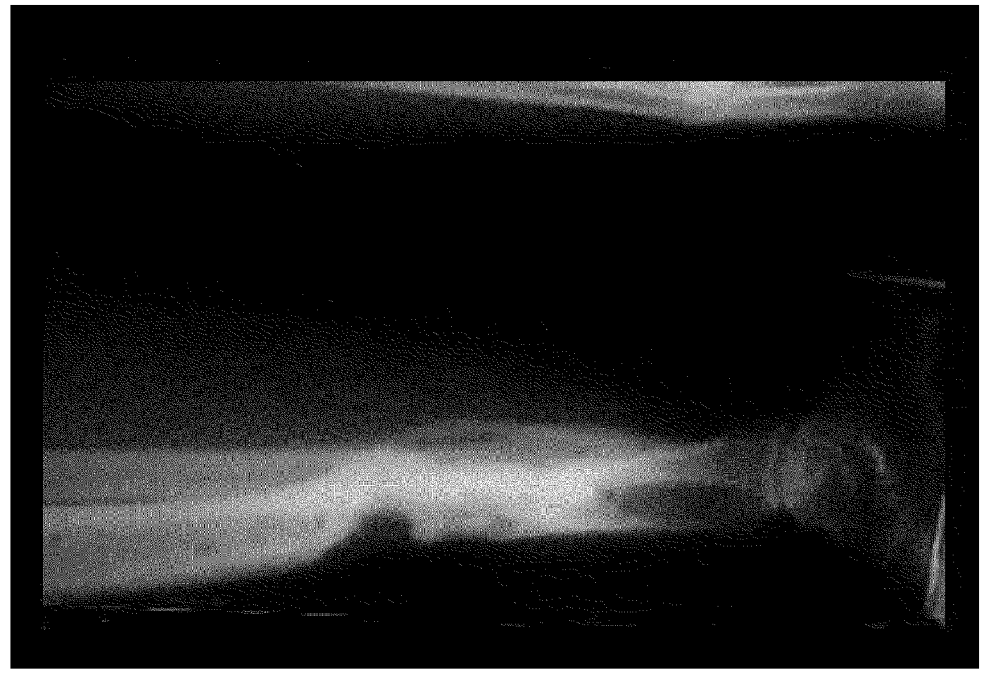
FIG. 4A is an X-ray of the lower leg of a 41 year old patient suffering from pseudo-arthrosis with infection prior to treatment.
Figure 5A:
FIG. 5A is a picture of the lower leg of a patient suffering from pseudo arthosis with infection prior to treatment.
Figure 5B:
FIG. 5B is a picture of the lower leg of a patient suffering from pseudo arthosis with infection after treatment in accordance with the present invention.
Figure 6B:
FIG. 6B is an X-ray of the arm of a 9 year old patient suffering from pseudo arthosis with infection after treatment in accordance with the present invention.
Figure 6A:
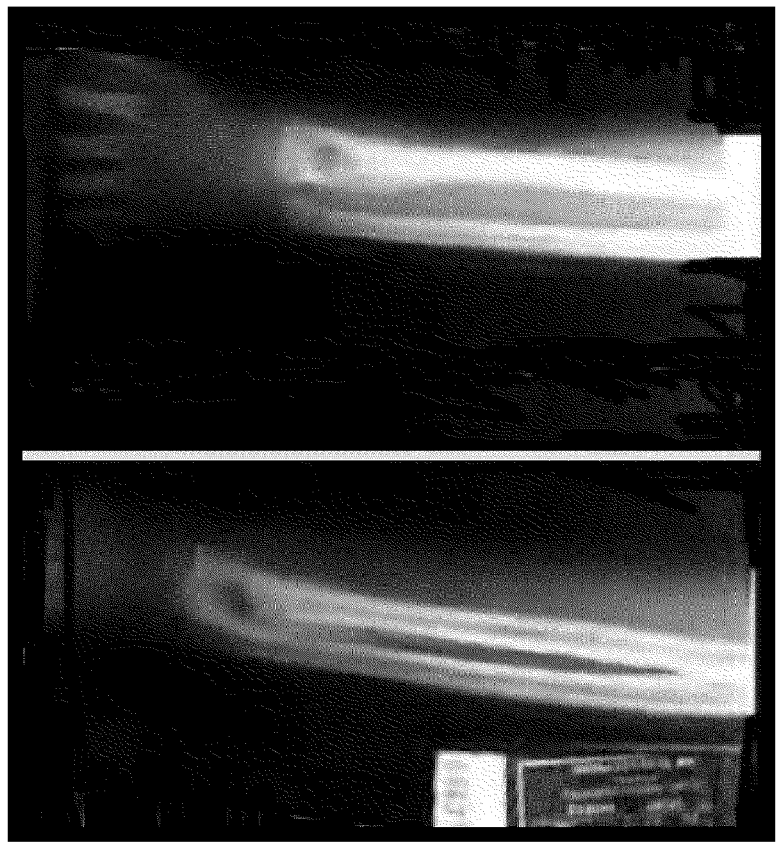
FIG. 6A is an X-ray of the arm of a 9 year old patient suffering from pseudo arthosis with infection prior to treatment
Figure 7B:
FIG. 7B is an X-ray of the femur of a 24 year old patient suffering from pseudoarthrosis with infection after treatment in accordance with the present invention.
Figure 7A:
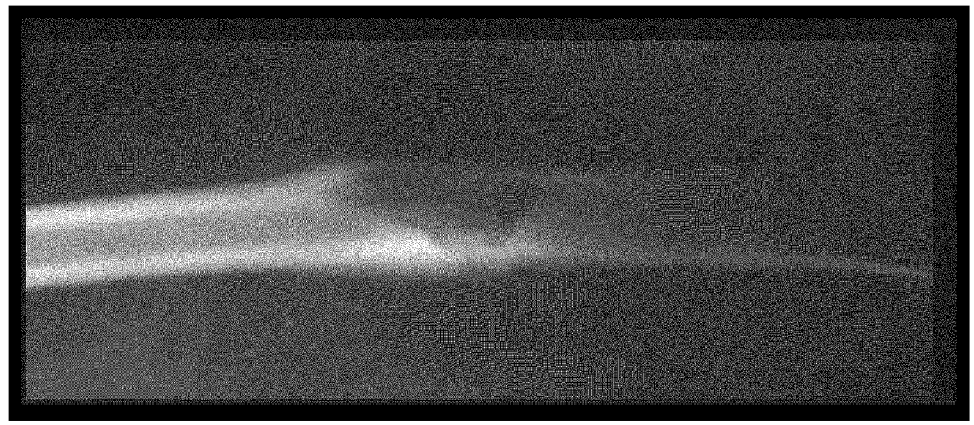
FIG. 7A is an X-ray of the femur of a 24 year old patient suffering from pseudoarthrosis with infection prior to treatment.

Group II:

This clinical trial group included 15 patients diagnosed with Pseudoarthrosis with infection. The patients had one capsule or tablet per day during 3 consecutive months. The results are as follows:

38% (6 patients) responded within 8 weeks
23% (3 patients) responder within 6 weeks
46% (6 patients) responded within 12 weeks The average number of weeks to obtain visible clinical and radiological changes and disappearance of any bacterial presence was 7.3 weeks. The control was without clinical or radiological changes. FIG. 2A is an X-ray of a 36 year old patient prior to treatment. FIG. 2B is an X-ray of the same 36 year old patient after 8 weeks of treatment using the herbal formulation. FIG. 3A is an X-ray of a 31 year old patient prior to treatment. FIG. 3A is an X-ray of the same 31 year old patient after 8 weeks of treatment using the herbal formulation. FIG. 4A is an X-ray of a 41 year old patient prior to treatment. FIG. 4B is an X-ray of the same 41 year old patient after 8 weeks of treatment using the herbal formulation. FIG. 5A is a picture of the leg of a 57 year old patient prior to treatment. FIG. 5B is a picture of the same 57 year old patient after 8 weeks of treatment using the herbal formulation. FIG. 6A is an X-ray of a 9 year old patient prior to treatment. FIG. 6B is an X-ray of the same 9 year old patient after 8 weeks of treatment using the herbal formulation. FIG. 7A is an X-ray of a 24 year old patient prior to treatment. FIG. 7B is an X-ray of the same 24 year old patient after 8 weeks of treatment using the herbal formulation.

Figure 8B:
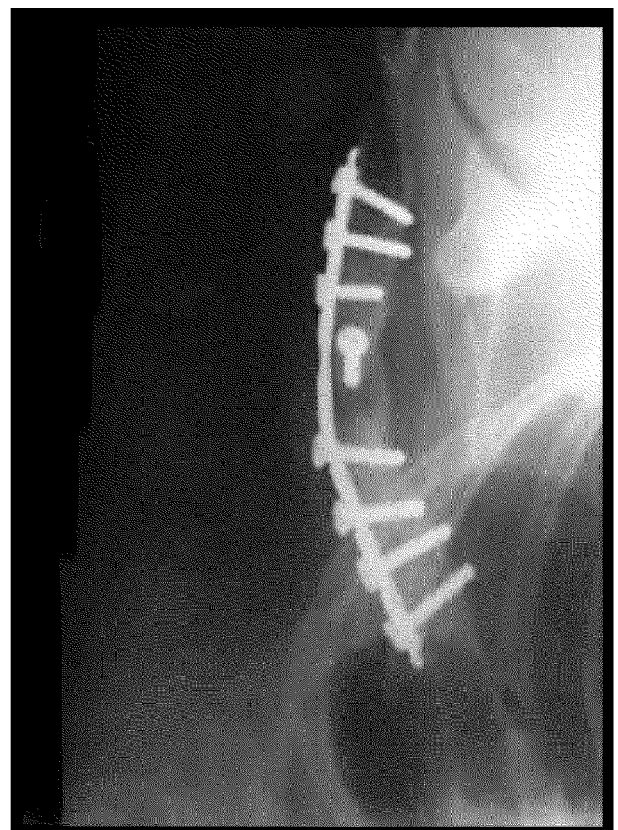
FIG. 8B is an X-ray of the clavicle of a 43 year old patient suffering from delay of surgical consolidation after treatment in accordance with the present invention.
Figure 8A:
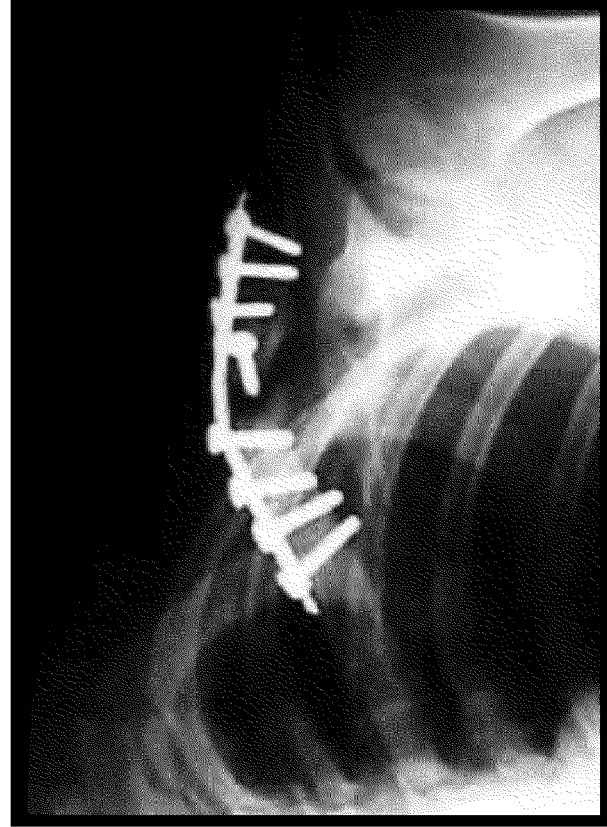
FIG. 8A is an X-ray of the clavicle of a 43 year old patient suffering from delay of surgical consolidation prior to treatment.

Group III:

This clinical trial group included 24 patients having delay of consolidation in post-surgical fractures. The herbal formulation provided which ones consolidated. The patients had one capsule or tablet per day during 3 consecutive months. The results are as follows:

25% (6 patients) merited 3 weeks
4% (1 patient) merited at 5 weeks
58% (14 patients) merited at 6 weeks
13% (3 patients) merited at 8 weeks The average number of weeks for obtaining consolidation, visible radiological in a significant manner was 5.5 weeks. The control was 12 weeks for visualization of consolidation, radiological verifiable. FIG. 8A shows an X-ray of the clavicle of a 43 year old patient prior to treatment. FIG. 8B is an X-ray of the same 43 year old patient after 8 weeks of treatment using the herbal formulation.

Group IV

This clinical trial group included 44 patients having simple and/or pathological fractures. The herbal formulation provided no surgical fractures and show which ones consolidated. The patients had one capsule or tablet per day during 3 consecutive months. The results are as follows:

95% (42 patients) merited 4 weeks
5% (2 patients) merited 2 weeks

Figure 9B:
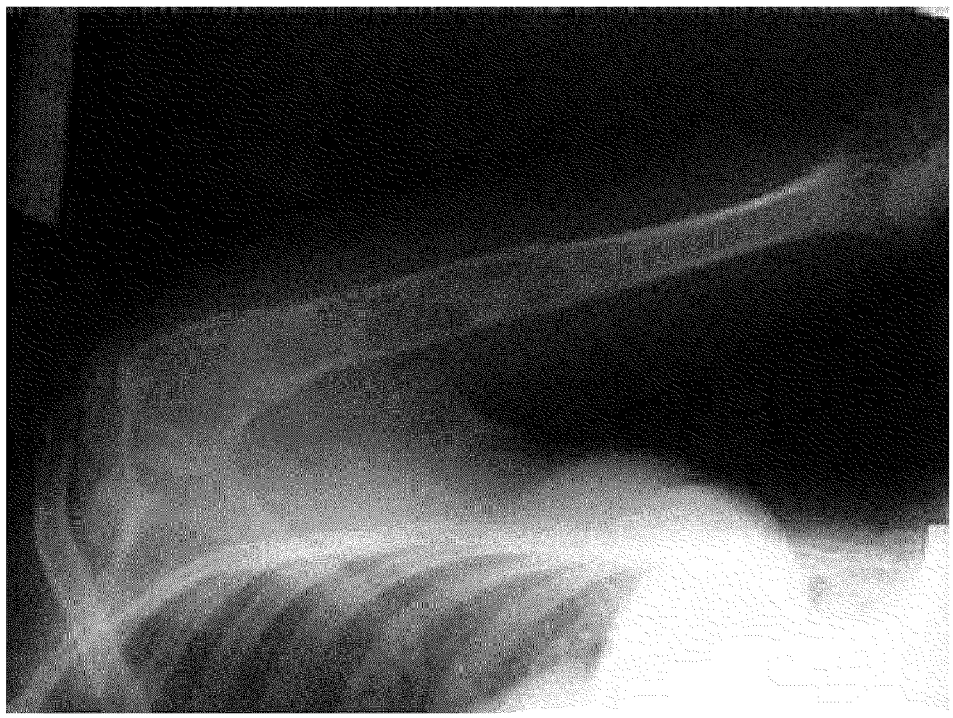
FIG. 9B is an X-ray of a humerus of a 28 year old patient suffering from simple fractures not surgical after treatment in accordance with the present invention.
Figure 9A:
FIG. 9A is an X-ray of a humerus of a 28 year old patient suffering from simple fractures not surgical prior to treatment.

The average number of weeks for the radiological visualization of the consolidation was 3 weeks. The control was 12 weeks for the radiological visualization of the consolidation. FIG. 9A shows an X-ray of the humerus of a 28 year old patient prior to treatment. FIG. 9B is an X-ray of the same 28 year old patient after 2 weeks of treatment using the herbal formulation.

Group V:

This clinical trial group included one patients having Osteogenesis Imperfecta. The herbal formulation consolidated surgical fractures with outline without surgery. The patients had one capsule or tablet per day during 3 consecutive months. The results are as follows:

100% (1) merited 12 weeks

Figure 10B:
FIG. 10B is an X-ray of a femur of a 57 year old patient suffering from osteogenesis imperfecta after treatment in accordance with the present invention.
Figure 10A:
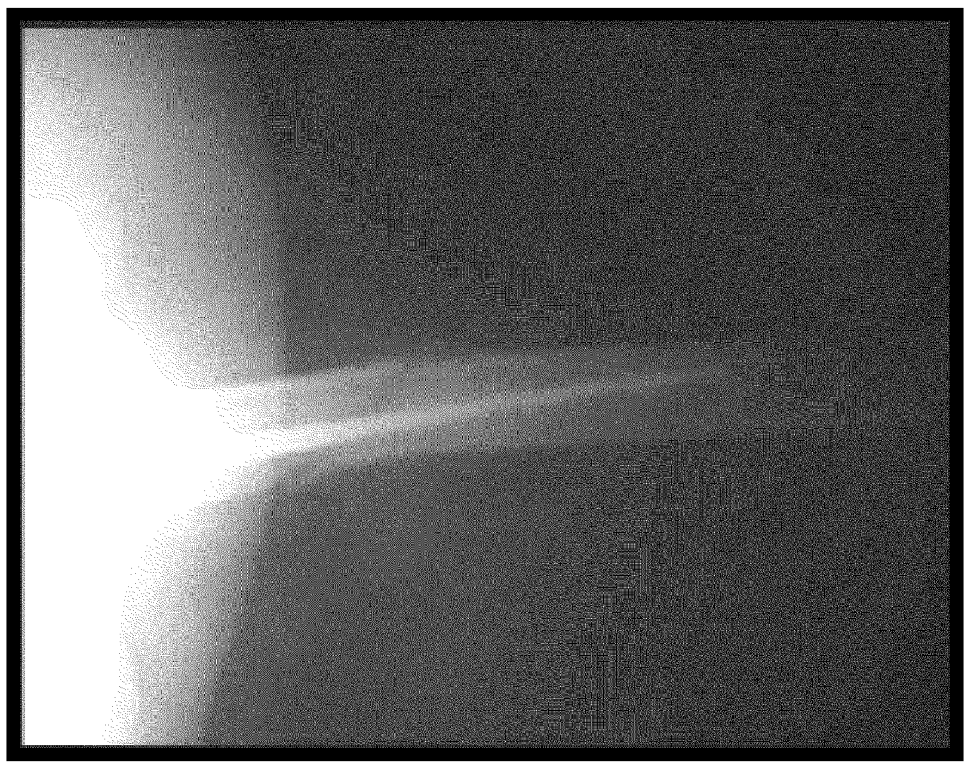
FIG. 10A is an X-ray of a femur of a 57 year old patient suffering from osteogenesis imperfecta prior to treatment.

The number of weeks for the radiological visualization of callus osseous was 4 weeks and both fractures consolidated at 12 weeks. The control was without significant radiological changes. FIG. 10A shows the X-ray of the femur of a 57 year old patient prior to treatment. FIG. 10B is an X-ray of the same 57 year old patient after 8 weeks of treatment using the herbal formulation.

Figure 11B:
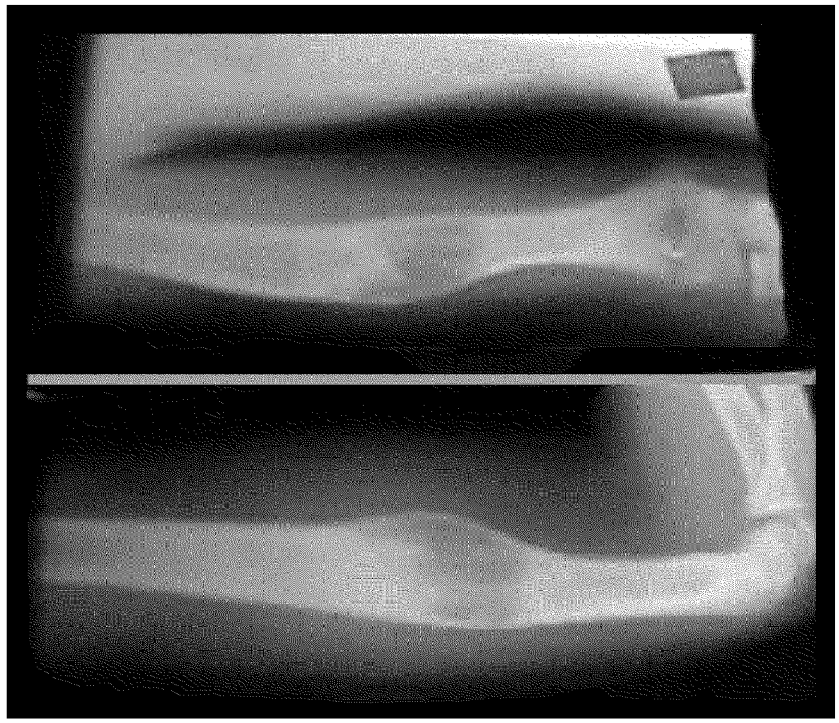
FIG. 11B is an X-ray of the humerus of a 12 year old patient that has osseum tumors after treatment in accordance with the present invention.
Figure 11A:
FIG. 11A is an X-ray of the humerus of a 12 year old patient that has osseum tumors prior to treatment.
Figure 12B:
FIG. 12B is an X-ray of a joint in a 14 year old patient that has osseum tumors after treatment in accordance with the present invention.
Figure 12A:
FIG. 12A is an X-ray of a joint in a 14 year old patient that has osseum tumors prior to treatment
Figure 13B:
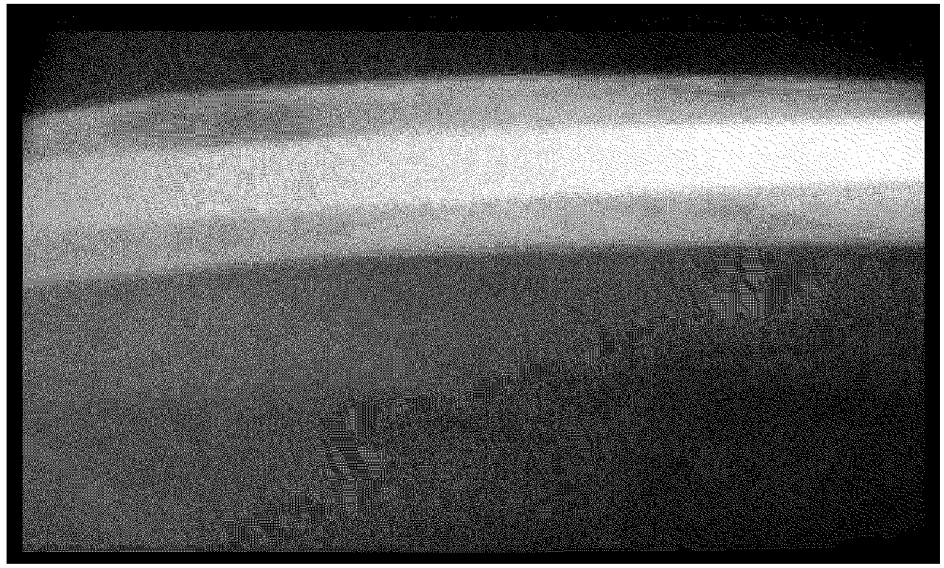
FIG. 13B is an X-ray of a bone in a 52 year old patient that has osseum tumors after treatment in accordance with the present invention.
Figure 13A:
FIG. 13A is an X-ray of a bone in a 52 year old patient that has osseum tumors prior to treatment.
Figure 14B:
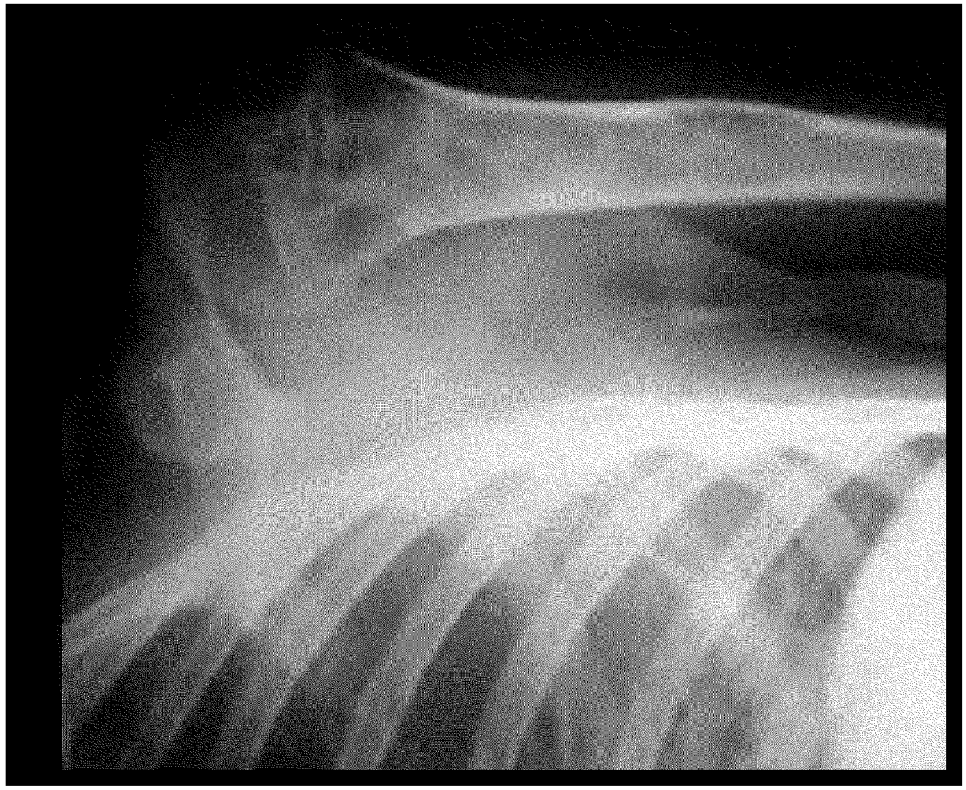
FIG. 14B is an X-ray of the humerus of a 11 year old patient that has osseum tumors after treatment in accordance with the present invention.
Figure 14A:
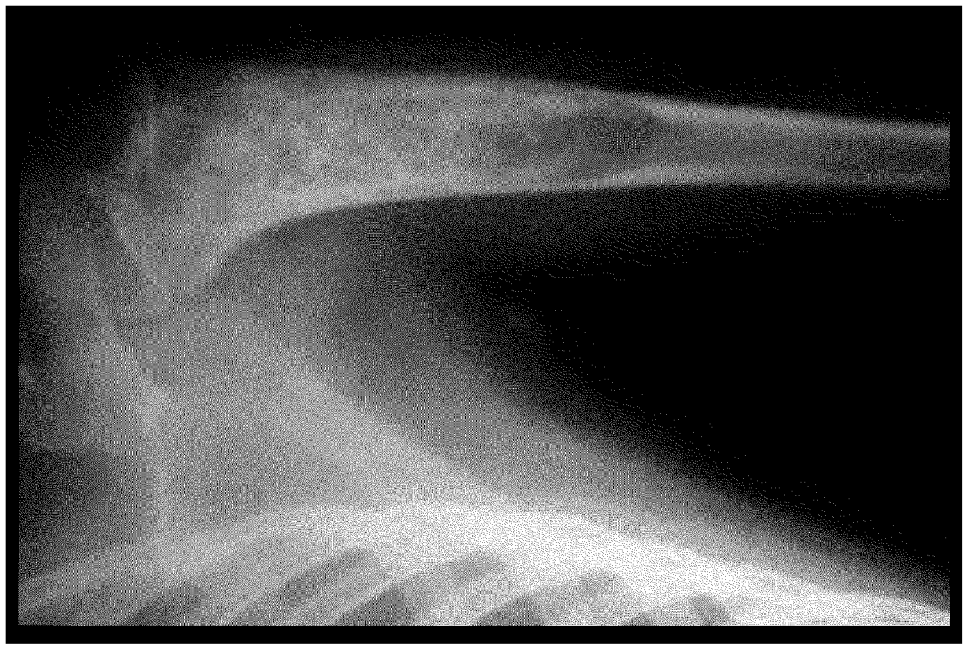
FIG. 14A is an X-ray of the humerus of a 11 year old patient that has osseum tumors prior to treatment.

Group VI:

This clinical trial group included 4 patients having osseous tumors. The herbal formulation regenerated on average 90% of the osseous tissue. The patients had one capsule or tablet per day during 3 months up to one year. The results are as follows:

25% (1 patient) showed regeneration on 99% in 14 weeks
25% (1 patient) showed regeneration on 80% in 40 weeks
25% (1 patient) showed regeneration on 90% in 44 weeks
25% (1 patient) showed regeneration on 90% in 72 weeks The average regeneration was 11 months. The control showed increases of the degenerative changes. FIG. 11A shows the X-ray of a humerus of a 12 year old patient prior to treatment. FIG. 11B shows an X-ray of the same 12 year old patient after 22 weeks of treatment using the herbal formulation. FIG. 12A shows the X-ray of a joint in a 14 year old patient prior to treatment. FIG. 12B shows an X-ray of the same 14 year old patient after 8 weeks of treatment using the herbal formulation. FIG. 13A shows the X-ray of a femur of a 52 year old patient prior to treatment. FIG. 13B shows an X-ray of the same 52 year old patient after 48 weeks of treatment using the herbal formulation. It is also shown in case 3 of Group VI of the trial that the herbal formulation has anti-litical properties. Due to the biological intringuilish, structural BRCA1 gene located in the same locus and responsible for the development of cancer (multiple myeloma) is regulated to permit the divorce of cell B and osteoclasts (Interlukine 6) which association produces the litic condition of the bone in this pathology. FIG. 14A shows the X-ray of a humerus of a 11 year old patient prior to treatment. FIG. 14B shows an X-ray of the same 11 year old patient after 10 weeks of treatment using the herbal formulation.

Group VII

Figure 15B:
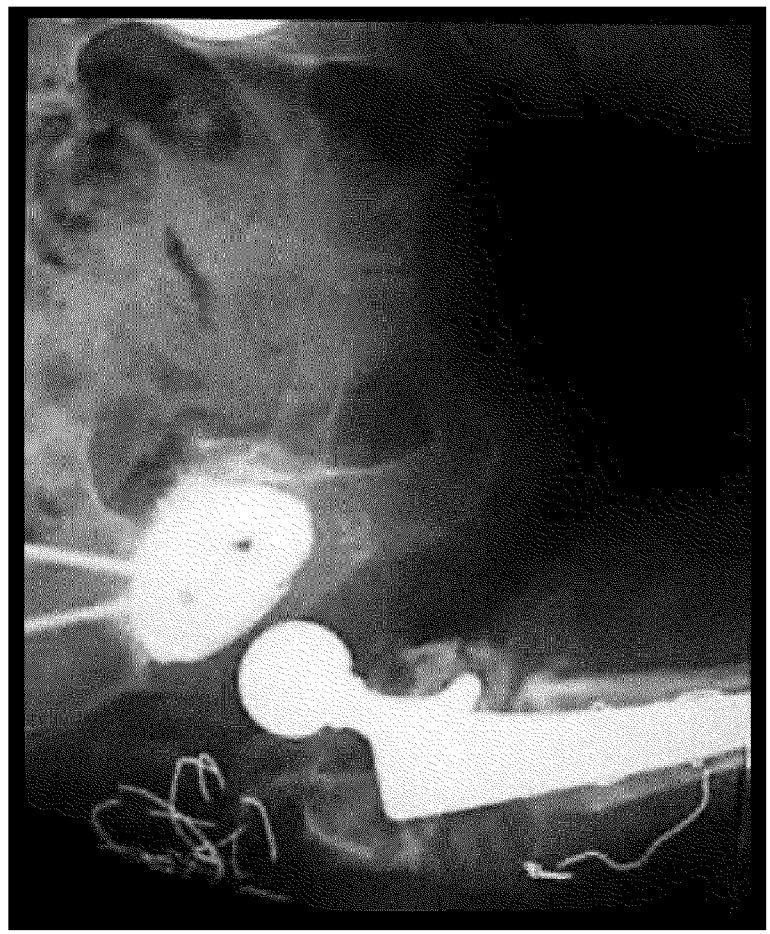
FIG. 15B is an X-ray of a femur of an 86 year old patient that has hip prosthesis tumors after treatment in accordance with the present invention.
Figure 15A:
FIG. 15A is an X-ray of a femur of an 86 year old patient that has hip prosthesis prior to treatment.

This clinical trial included a patient having entire prosthesis of hip to form new bone tissue. The patient regenerated 90% of bony tissue in an average of about 10 months. The patients had one capsule or tablet every 2 days during a year. The control showed no changes. FIG. 15A shows the X-ray of a hip prosthetic of an 86 year old patient prior to using the herbal formulation. FIG. 15B shows an X-ray of the same 86 year old patient after 96 weeks of treatment using the herbal formulation.

Group VIII

This clinical trial included a group of 3 patients diagnosed with osteoporosis and osteopenia. The treatment increased mineral thickness and diminished the risk of break. The patients had one capsule or tablet every 2 days during a year.

100% (3 patients) increased DMO in 52 weeks

The average increase in bone density (DMO) was 4.5%. The control decreased DMO 2.5%.

The following information is submitted based on the results of studies conducted on individual patients:

A chronological comparison of a patient was diagnosed. The study of bone densitometry practiced on Mar. 24, 1998 was compared with the study dated Nov. 27, 1995, appreciated the following changes in the Bone mineral Density:

|  | 95 | 98 | Difference |
|---|---|---|---|
| Lumbar column | 11 | 08 | +03% |
| (Femur) | 17 | 12 | +05% |

It is appreciated an increase in the DMO (bone density) in the femur and lumbar column. It was suggested to continue the specific herbal formulation therapeutic measurements to correct the risk factor and repeat this study in 1 year. The regime used by the patients of this group is a capsule or tablet every 2 days. The patient was subjected to bone densitometry on Jul. 7, 2000 utilizing lunar DPX with a program version 3.65 in accordance with the actual skill; analyzing mineral bone density (DMO) expressed in grs/cm$^2$ in the areas of the lumbar column in projection (anteroposterior) and femur in the regions of (Troncanter), neck and wards. This information was processed, analyzed and compared with the population of reference of young adult and people of the same age obtaining the percentage of osseous loss, the T-score (deviation standard) and calculating the risk relative of fracture (RR). In continuation the results are expressed in summarized form:

| Area | DMO (grs/cm2) | % Osseous Loss | R.R. | T-Score |
|---|---|---|---|---|
| AP Column | 1.041 | 12% | Moderated | −1.16 |
| Femur | 0.844 | 14% | Moderated | −1.13 |

Additionally the patient was asked various questions regarding the factors of risk for osteoporosis with the following results:

| Low ingestion of calcium | [ ] | Therapy with steroids | [ ] |
|---|---|---|---|
| Early Menopause | [x] | Bad absorption inst. | [ ] |
| Oofereotomia | [ ] | Diabetes | [ ] |

-continued

| | | | |
|---|---|---|---|
| Thyroid illness | [ ] | Smoking | [ ] |
| Hist. Fam. of Osteoporosis | [ ] | Alcohol ingestion | [ ] |
| Sedentary lifestyle | [x] | Coffee ingestion | [ ] |

The results reveal a moderate decrease of the DMO level of tissue osseous (trabecular), and cortical, reflecting a moderate fracture. It is suggested that the patient modify lifestyle to correct risk factors and proceed with specific therapeutic measurements to order to improve osseous mass and prevent falls. It is recommended that the patient repeat the study within a (1) year or in accordance with clinical evolution. The bone density of x-rays of dual energy of hip and column for the high (reproductively) low dosage of radiation and high precision constructs a standard for the evaluation of a patient with risk of Osteoporosis and permits the differentiation between the changes of osseous observed in the bone (trabecular) and cortical, no evaluation for preferred measurements.

The follow results were obtained for another patient

| Date Scan | Region | DMO g/cm2 | % NJ | % SE |
|---|---|---|---|---|
| 14 Oct. 1998 | L1-L4 | 1.020 | 86 | 106 |
| 07 Jul. 2000 | L1-L4 | 1.041 | 88 | 108 |
| 14 Oct. 1998 | Neck-I | 0.820 | 84 | 104 |
| 07 Jul. 2000 | Neck-I | 0.844 | 86 | 106 |

It is appreciated that an increase of the mineral bone density levels of the studied area. It is suggested to continue the specific therapeutic measurement, correct factor of risk and repeat study in 1 year or in accordance with clinical evolution.

Another 72 year old patient was evaluated utilizing bone densitometry mark provided by the Lunar DPK PLUS. The results of the study are expressed as density of bone mineral (DMO), in grs/cm$^2$ releasing a loss percentage of DMO with a healthy population of the same sex between 20 and 40 years of age, a reference to the people in the same group, being specified of existing, the risk relative of fracture and presence of osteoporosis according to the realized study. The images awarded in the reports so with ends of orientation and should not be considered like diagnostic elements, for which it is recommended the utilization of radiological studies type (Rx. TAC and RM). The evaluation of the Lumbar AP column shows a DMO of 0.840 (Li-L2) grs/cm$^2$), of which corresponds to a demineralization of 27% with respect to a population of 20 to 40 years of age, and with 7% with respect to identical groups. Its Value Z-2.59. Estimated status is osteoporotico, with risk relative of moderate fracture susceptible increased in L1, L2, in status and risk described evidences of the Osteoartosico process. Especially in L3, L4, L5 with explains the apparent major DMO vertebral collapse must be discarded. The evaluation of the hip (femur proximal) shows a DMO of 0.690 grs/cm$^2$, of which corresponds to a demineralization of 30% with respect to a population of 20 to 40 years of age, and which corresponds to 10% with respect to identical group. It's Value Z-2.42. Estimated status is Osteopenico with risk relative of moderate fracture susceptible increased in triangle of wards, in status Osteoporotico and describe risks. It is suggested to avoid factors of risk, maintaining an adequate ingestion of calcium, and preventive treatment, antiresortive, according to criterion of the medical treatment. A bone density of the control in 1 year permits determination of the rate of modification of the bone mass.

The above patient two years later at the age of 74 was subjected to bone densitometry that shows a DMO of 0.930 grs/cm2, which corresponds to a demineralization of 23% with respect to a population of 20 to 40 years of age, and with 0% with respect to identical group. Its value Z-2.25. Estimated status Osteoporotico, with risk relative of moderate fracture susceptible increased in L1, L2, in status Osteoporotico and moderate risk. Shows a DMO of 0.700 grs, of which corresponds to a demineralization of 29% with respect to a population of 20 to 40 years of age, and which 6% with respect to identical group. It's Value Z-2.34. Estimated status Osteopenico with risk relative of moderate fracture susceptible increased in triangle of T. wards and trocanter, in status Osteoporotico and moderate risk. A bone density is suggested of the control in 1 year to permit determination of the rate of modification of the osseous mass.

The study explored the bone density using Marca Norland XR-26 expressed the values of Density Mineral Osseous in gr/cm2, loss percentage (%) with respect to a population (Latin) of age, loss with respect to a population of 20 to 40 years of age and the risk of fracture, specified in every region explored. The conclusion diagnosis is release in accordance with the classification recommended by the World Organization of Health 1994.

1. Exploration of Femur
   The Bone Mineral Density is 0.728 gr/cm2 corresponding to a demineralization of 28.5% in relation to a population of 20 to 40 years of age, and with 17% with respect to population of the same age.
   Risk of fracture: 6.2 time higher than the population of reference (area of higher risk triangle of wards).
   Conclusion: Advanced Osteopenia
   Note: it appreciates a profit of bone mass of 3.6% year
2. Exploration of Lumbar AP Column
   The Bone Mineral Density is 0.857 gr/cm2 corresponding to a demineralization of 26.4% in relation to a population of 20 to 40 years of age, and with 16.5% with respect to population of the same age.
   Risk of fracture: 3.6 times higher than the general population (area of highest risk: in L2)
   Conclusion: Osteopenia
   Note: it appreciates a profit of osea mass of 0.4%/year

CONCLUSION

The results obtained with the oral administration of the herbal formulation shows the new bone formation in a very fast manner than the groups of control. In all infected fractures, the herbal formulation provided for the disappearance of the presence of infection, where it was, and started the bone reorganization. In the 21 days of treatment, the herbal formulation provides for the presence of major osseous trabeculation and begins the formation of osseous callus, radiology visible, in simple fractures and improved health in infected patients. Finally, between 45 and 60 days bacteria starts to disappear from cultures and antibiograms, to give chance for a new osseous formation.

It is noticeably significant in this study when comparing the results obtained with the administration of the treatment in the experimental group in relation of the results obtained in the control group (without treatment). It is also significant that neither of the two groups showed adverse reactions which deduces that the use of the herbal formulation is innocuous. It is mentionable to note the remodeling speed in the Osteogenesis imperfecta.

The herbal formulation stimulates the osseous regeneration to superior levels in patients compared with the osseous regeneration obtained without its use. This suggests that it can modify physical chemistry and biological properties, also, has genetic action that favors the formation of an osseous matrix with better capacity for invasion and migration of osteoprogeneritoras cells. This translates into providing a patient with the ability to promptly reinstate in daily life. Finally, based on these results, it is suggested that therapeutic application of the herbal formulation in the resolution of defects and osseous pathologies is significant.

It should be understood that changes and modification in the specifically described embodiment of the present invention can be carried out without departing from the scope of the present invention which is defined by the following claims:

We claim:

1. An herbal formulation that catalyzes the formation of osseum callus and new bone tissue when administered to a patient comprising
    a) 0.02-0.05 cc *Symphytum Officinalis* extract,
    b) 0.01-0.04 cc *Phytolacca Decandra* extract and
    c) magnesium chloride USP.
2. The herbal formulation of claim 1, further comprising
    d) absolute ethanol, and
    e) sugars selected from the group consisting of saccharose and lactose.
3. The herbal formulation of claim 2, comprising
    a) 0.02 cc *Symphytum Officinalis* extract;
    b) 0.01 cc *Phytolacca Decandra* extract;
    c) 2 grams magnesium chloride USP,
    d) 100 cc absolute ethanol, and
    e) 1000 grams sugars selected from the group consisting of saccharose and lactose.
4. The herbal formulation of claim 1, wherein said herbal formulation is in a form selected from the group consisting of capsules and tablets.
5. The herbal formulation of claim 1, wherein said *Symphytum Officinalis* extract and said *Phytolacca Decandra* extract are the only herbal ingredients in said herbal formulation.
6. The herbal formulation of claim 1, wherein said herbal formulation is provided as a topical application.

* * * * *